United States Patent
Germano

(12) 
(10) Patent No.: US 6,503,506 B1
(45) Date of Patent: Jan. 7, 2003

(54) NUTRIENT THERAPY FOR IMMUNO-COMPROMISED PATIENTS

(75) Inventor: Carl Germano, New City, NY (US)

(73) Assignee: Millenium Biotechnologies, Inc., Barnardsville, NJ (US)

( * ) Notice: Subject to any disclaimer, the term of this patent is extended or adjusted under 35 U.S.C. 154(b) by 0 days.

(21) Appl. No.: 09/927,174

(22) Filed: Aug. 10, 2001

(51) Int. Cl.[7] ............................................. A61K 38/44
(52) U.S. Cl. ..................................... 424/94.3; 514/561
(58) Field of Search ......................... 424/94.3; 514/561

(56) References Cited

U.S. PATENT DOCUMENTS 6,045,809 A    4/2000   Postaire et al. ............. 424/400

*Primary Examiner*—Jean C. Witz
(74) *Attorney, Agent, or Firm*—Schweitzer Cornman Gross & Bondell LLP

(57) ABSTRACT

A nutritional supplement is taught for treating chronic debilitating diseases such as HIV/AIDS to overcome conditions of oxidative stress, decreased lean muscle mass, decreased energy production (mitochondrial failure) and support immune function. It comprises orally administrable superoxide dismutase (SOD), preferably SOD/GLIADIN, in combination with other antioxidant/immune support components (Beta Glucans, Nucleotides, Fruit Polyphenols); High Immunoglobin Whey; (undenatured whey), Ornithine alpha ketoglutarate (OKG), Branched Chain Amino Acids and Glutamine to reduce loss of lean muscle mass; and Coenzyme Q 10, D-Ribose and L-Carnitine to provide energy support (decrease mitochondrial failure).

11 Claims, No Drawings

NUTRIENT THERAPY FOR IMMUNO-COMPROMISED PATIENTS

BACKGROUND OF THE INVENTION

Unfortunately there appears to be a growing number of people suffering from chronic debilitating diseases characterized by muscle tissue wasting, decreased energy and oxidative stress and immune impairment.

Most dramatic of such disease is the major increase in HIV presently infecting over 50 million people. Currently approximately 22 million people have died from the consequences of HIV induced Acquired Immune Deficiency Syndrome (AIDS). HIV attacks the human immune system, weakening the body and reducing the patient's ability to ward off opportunistic infections, ultimately rendering him/her defenseless against diseases that usually and under normal circumstances can be successfully treated. There is no cure for AIDS.

Over the years a sizable array of vaccines, antiretroviral drugs, such as AZT and other viral suppressive compounds, have been developed that seek to—if not defeat, at least control the rate at which HIV replicates and thereby slow the progression of the disease, or even arrest it. However, most of these drugs to be effective have to be taken in combination with complicated regimes that need to be followed meticulously and indefinitely. More importantly, the toxic nature of these drugs leads to further decreases in host defense, energy production and increases in oxidative stress furthering the development of the disease. These drugs are expensive and not affordable by many if not most HIV infected persons. Furthermore, even if available and affordable, there presently are no reliable data on the side effects of such long term therapy, or HIV's capacity to mutate into drug resistant strains.

To those infected with AIDS and many other chronic debilitating diseases, wasting syndrome is a very real part of their every day life. Wasting is the term used for the loss of lean muscle mass due to the virus placing additional nutritional demands on the body. These stresses can diminish appetite causing the body to use protein and other nutrients from muscle stores that help the body function correctly. As a result of this, muscles become smaller, weaker and less flexible. Eventually when muscle loss becomes significant, the ability for the body to function normally and combat other common infection greatly diminishes.

In recent years, a considerable amount of information on the spectrum of clinical consequences of HIV infection has been accumulated. The most striking characteristics of this disease include severe malnutrition and wasting syndrome. Such malnutrition involves both changes in overall body composition as well as deficiencies of specific nutrients. As HIV infection progresses to AIDS, a significant result is under-nutrition producing the added effects of starvation, a potent immuno-suppressant. Nutritional support could thus help maintain health in the HIV+ patient by replacing lost nutrients, compensating for nutritional damage done by the retrovirus-induced immunodeficiency, and stimulating the remaining immune system and cells for better host defenses. The medical community generally agrees that there remains an urgent need for interventions, including inexpensive nutrient therapies, which serve as an adjunct to current medical treatment for persons with HIV/AIDS (PWAs).

It has been shown that the course of infection is influenced by different factors including age, genetics, environmental, opportunistic infections, therapy and nutritional status. Among these, there is considerable evidence to suggest important links between nutrients, oxidative stress and HIV infection. Alterations of nutrients and increased oxidative stress associated with inadequate antioxidant intake have been observed in HIV infected subjects. Such nutrient depletions may influence immunological function, viral replication, carcinogenesis, development of cardiomyopathy and resistance to infection.

Additionally adherence is also an extremely important issue for nutritional supplements. If the product is distasteful or unpleasant to consume its use will not be repeated.

Unfortunately, there currently is no nutritional supplement on the market that addresses these major issues and conditions, such as oxidative stress, decreased lean muscle mass and weight, and mitochondrial failure (decreased energy production), associated with HIV/AIDS and other chronic debilitating diseases.

BRIEF DESCRIPTION OF THE INVENTION

The present nutritional support composition addresses the needs of those whose immune systems are compromised through HIV/AIDS and other chronic debilitating diseases through a multiprong approach designed to:

Decrease oxidation stress
Help restore lean muscle mass
Up-regulate/increase energy production (decrease mitochondria failure)
Support Immune System Specifically the present composition comprises in combination:

1. Orally administrative superoxide dismutase (hereinafter referred to as SOD) in combination with a lipid or protein carrier derived from plants to serve as an antioxidant support.

Particularly preferred is the protein prolamine derived from cereals, and especially SOD/Gliadin.

The orally administrable SOD component may be supplemented by other antioxidant components—Beta Glucans, Nucleotides and Fruit Polyphenols.

2. A mitochondrial/energy support component selected from the group consisting of Coenzyme Q10, D-Ribose and L-Carnitine 3. A component for maintaining lean muscle mass comprising a member of the group Ornithine alpha ketoglutarate (OKG) and High Immunoglobulin Whey (undenatured whey), which may be supplemental by other components such as Branched Chain Amino Acids, Instantized Casein, and Glutamine.

In addition to the foregoing functions, SOD/Gliadin, Beta Glucans, Coenzyme Q10, Nucleotides, Glutamine and Undenatured Whey Protein also help to support immune function.

The present composition will not interfere with or react with current drug therapies for treating HIV/AIDS or cancer. It is easily miscible with water, milk or juices to completely dissolve. It is easily blendable with flavoring agents to overcome poor adherence plaguing other nutritional products. Flavors such as Dutch Chocolate, Wild Berry and Vanilla Honey Caramel have been produced.

While certain of the above components have been used therapeutically, the present invention distinguishes over such prior art by:

Providing a multicomponent system approach to treating chronic debilitating diseases, and Providing the first orally bioavailable form of SOD in combination with other synergistic nutritional components

DETAILED DESCRIPTION OF THE INVENTION

1) Antioxidant Support

The primary agent is orally administrable superoxide dismutase (SOD) in combination with a lipid or protein carrier derived from plants. A detailed description of such an antioxidant will be found in U.S. Pat. No. 6,045,809 issued Apr. 4, 2000 whose specification is hereby incorporated by reference. Such SOD compositions have good bioavailability and are therefore therapeutically effective.

In one embodiment the proteins are selected form the group consisting of prolamines and polymer films based on prolamines. The prolamines are preferably of vegetable origin and can be obtained from different cereals, especially wheat, rye, barley, oats, rice, millet and maize. Particularly preferred is gliadin derived from wheat. SOD/Gliadin, which has recently become available commercially, is especially preferred in the instant composition.

In another embodiment, the plant lipids are preferably selected from the group consisting of ceramides, phospholipids tylacoids and diacylglycerols. Particularly desired are ceramides of vegetable origin derived from cereals, especially wheat.

SOD (Superoxide Dismutase)

In the past, SOD was a very popular supplement acting as a master cellular defense enzyme. Unfortunately, taking this supplement orally yielded little if any benefit since it is easily destroyed in the GI tract via digestive enzymes. Hence, the use of injectable SOD from bovine sources was the form of choice in most of the published studies. Today, after extensive research and development, SOD microencapsulated with Gliadin (SOD/Gliadin) has been shown to be absorbed intact orally as well as up-regulate other defense enzymes in the cell: Much of the research available on SOD and the immune system centers on HIV and antioxidants. Because the immune system has a more general function in the body, protecting us from disease and keeping us healthy in a myriad of ways, the clearest observations of the relationship between free radicals, SOD and immune system are found in studying HIV and AIDS. But research also makes associations between oxidative stress and the overall strength of the immune system. It has been found that SOD can offset the damage done by free radicals, prevent damage to the immune system, and consequently help delay or prevent the onset of degenerative diseases and immune-related conditions like HIV and AIDS.

Studies show that:

Adding SOD to infected white blood cells from patients with HIV showed that SOD slowed down the spread of HIV through the infected cells. The reducing effect of SOD on superoxide seems to affect not only the level of HIV in the white blood cells, but also the rate of transmission of the virus between cells.

SOD may slow the expression of HIV to AIDS by demonstrating that SOD reduced the levels of the virus core protein, an indicator of its presence in the cells.

SOD can enhance immunity. The presence of free radicals appears to contribute to the suppression of the immune system. As part of the immune response free radicals like superoxide are produced, but these free radicals can cause tissue and immune system damage. SOD can counter the effects of free radicals, thereby enhancing immune function.

Additional antioxidant support compounds (termed AASC for convenience) may also be present in the instant compositions. Such AASC compositions are selected from the group consisting of Beta Glucans and Fruit Polyphenols. The latter are polyphenolics from prune, apple, cherry, pomegranate and nectarine.

Beta Glucans

Our immune system is our primary natural defense against disease and aging. Beta Glucans are fuel for our immune system. Specifically, beta-1,3-D-glucans are unique ingredients derived from yeast cell walls and oats. Once activated by Beta-1,3-D-glucans, the immune system creates "an arsenal of defense" against viral, bacterial, fungal, parasitic or neoplastic assailants. Unlike other immune enhancing supplements and pharmacological drugs, beta-1,3-D-glucans, trigger the immune response selectively where and pharmacological drugs, beta-1,3-D-glucans, trigger the immune response selectively where it starts-at the macrophage. Macrophages play an essential and pivotal role in the initiation and maintenance of the immune response.

Beta Glucans work by activating the macrophages, or immune cells, which trap and engulf foreign substances. Also, the activated cells start a cascade of events that cause the entire immune system to be alerted and mobilized, in an entirely naturally activated sequence. Beta Glucans also have powerful antioxidant attributes, with heightened free-radical scavenging activity to nutritionally enable the immune system to fight back against health invaders (pathogens) such as fungus, bacteria, viruses and parasites. While Beta Glucans can be derived from yeast and grain sources, activation of the immune response is best achieved from yeast cell wall and oat Beta Glucans.

Fruit Polyphenols

Polyphenolic Flavonoids (polyphenols) are compounds found in fruits, vegetables, tea, beans, and grains. Many of the flavonoid substances are known as "bioflavonoids". Polyphenolic flavonoids are very powerful antioxidants. Acting as antioxidants means that these flavonoids can help neutralize or inactivate free radicals before they damage the cells within the human body. Free radicals are natural by-products of daily metabolism and contribute to the aging process. Polyphenolic flavonoids have the following properties: immune-stimulating, anti-viral, anti-inflammatory, anti-mutagenic, cardio-protective, anti-allergic, and anti-carcinogenic. The anti-cancer activity of polyphenols has been correlated with the inhibition of colon, esophagus, lung, liver, breast and skin cancers.

2) Mitochondrial/energy Support

Key ingredients for providing this result are Coenzyme Q10, D-Ribose and L-Carnitine.

Coenzyme Q10

Coenzyme Q10 is an essential component of cellular energy production and respiration by participation in the mitochondrial electron transport system, which supplies energy (ATP) for a variety of physiological functions. Virtually every cell of the human body contains coenzyme Q10. Muscle mitochondria lack adequate coenzyme Q10 in people several degenerative diseases—from Alzheimer's to HIV/AIDS.

Additionally, COQ10 plays an important role in the preserving a healthy functioning immune system and modulates immunity. Blood levels of Coenzyme Q10 are founds to be low in individuals with HIV infection or AIDS. It is known that HIV/AIDS individuals have a deficiency of COQ10 and the deficiency increased with the severity of the disease. Human studies have demonstrated that COQ10 increases IgG and T4-lymphocytes when administered orally—clinically relevant for cancer, HIV/AIDS and other infectious diseases. Studies have shown that COQ10 has a positive influence on the host defense system. The T4/T8 ratios of lymphocytes are known to be low in patients with AIDS, ARC and malignancies. Oral administration of COQ10 revealed a positive increase in T4/T8 rations in HIV patients.

Individuals with HIV are characterized by both significant mitochondrial alterations and a dramatic tendency to undergo apoptosis. Coenzyme Q10 is an important antiapoptotic agent with promising potential for HIV therapy given the recent findings of apoptosis involvement toward AIDS progression of HIV infected individuals. Lastly, it has been shown that the antiviral nucleoside analogue zidovudine (AZT) depletes levels of mitochondrial DNA in muscle of patients on long-term therapy. Hence, COQ10 represents a critical therapeutic agent that may prevent neuronal mitochondrial dysfunction and apoptosis beneficial in the prevention of neurodegenerative processes in AIDS patients.

L-Carnitine

L-carnitine is an amino acid abundantly found in skeletal muscle. It functions primarily to regulate fat metabolism and also acts as a carrier of fatty acids into the mitochondria, where they are oxidized and converted into energy (ATP). Hence, it has the potential to improve mitochondrial function, fat metabolism, endurance and enhance the normal functioning of the heart. It has been established in the literature that serum Carnitine deficiency is common in patients with HIV/AIDS especially those on certain medications. AZT as used in the treatment of AIDS, causes mitochondrial myopathy. Additionally, since AZT is associated with mitochondrial destruction and impairment of mitochondrial DNA synthesis crucial to the pathogenesis of the disease, L-carnitine becomes a critical part of the nutritional support plan. The depletion of Carnitine which regulates the metabolism and function of peripheral nerves and mitochondrial DNA synthesis could contribute to the neurotoxicity of certain medications used to treat the disease as well as apoptosis and other significant symptoms. The depletion also is attributed to the clinical symptoms of myalgia and muscle weakness associated with the disease. Because Carnitine status is an important contributing factor to immune function in patients with AIDS, L-carnitine supplementation could have a role as a complimentary therapy for HIV infected individuals.

Ribose

Ribose is a carbohydrate, or sugar, used by all living cells and is an essential component in our body's energy production. As a new nutraceutical Ribose helps the body naturally restore its energy level. It's used by the body's cells to form the primary source of all the body's energy—ATP. ATP, the body's primary energy-carrying molecule, is necessary for maintenance of cellular integrity and function. Ribose plays a key role in the generations and recovery of ATP. Since cells and organs need adequate energy in order to maintain integrity and function, it is essential that the supply of ATP be replenished soon after it is consumed. Ribose provides benefits by quickly restoring energy levels in heart and skeletal muscles. Numerous studies demonstrate the ability of ribose to increase ATP levels and total adenine nucleotide recovery promoting skeletal and cardiac muscle energy metabolism. Since ATP production is hampered via mitochondrial dysfunction typically seen in AIDS, Ribose offers powerful complimentary support to other nutrients addressing energy depletion.

In addition to the foregoing components, supplemented effect is obtained by the added presence of Glutamine and SOD/Gliadin (also present due to their antioxidant effect), as well as medium chain triglycerides.

3) Agents for Maintaining Lean Muscle Mass

The key component for affecting this result is Ornithine Alpha Ketoglutarate (OKG).

Ornithine Alpha-Ketoglutarate

The amino acids Ornithine and glutamine are combined to form Ornithine Alpha-Ketoglutarate (OKG). Ornithine Alpha-Ketoglutarate affects human metabolism through three primary mechanisms: as an anabolic agent (releasing Human Growth Hormone, HGH), as an anti-catabolic agent, and as an inducer of protein synthesis. All three mechanisms contribute to muscular development and enhanced recovery. OKG has been used to treat patients suffering from burns, surgery, malnutrition and other trauma. Although the precise mechanism's unknown, OKG treatment decreases muscle protein catabolism (breakdown) and/or increases protein synthesis, in addition to promoting wound healing. OKG may promote the secretion of anabolic hormones such as insulin and growth hormone and increase amino acid metabolism (glutamine & arginine), which may help explain some of the clinical findings.

OKG supplements have been shown to improve protein retention, would repair, and immune function in hospitalized patients partly by increasing levels of anabolic (growth-promoting) hormones such growth hormone.

In addition to OKG, other agents for restoring lean muscle mass may be incorporated in the present compositions. Examples thereof are Undenatured Whey Protein, Instantized Casein and Branched Chain Amino Acids. The Nucleotides and Glutamine used for antioxidant support also contribute to restoring muscle mass.

Whey Protein

AIDS wasting is characterized by a loss of lean body mass including muscle and organ tissue, coupled with increased fat production. Loss of lean body mass can lead to muscle weakness, organ failure and sometimes death, making AIDS wasting a leading contributor to HIV related deaths. When it comes to nutritional support directed at maintain lean mass adequate calories and good quality protein are essential.

Whey protein concentrate has long been a favorite of body builders because it is the best protein for tissue repair and muscle building. The most commonly used criterion to measure quality of a protein in Biological Value (BV), which is the amount of nitrogen (body protein in grams) replaceable by 100 grams of protein in the adult diet. The higher its protein's BV, the higher its nitrogen retention. Proteins with the highest BV are the most potent lean tissue sparing and growth promoting proteins.

Whey is a complete protein, which contains all the essential and non-essential amino acids, and boasts the highest branched chain amino acid content found in nature. Whey also has the highest BV of any available protein. It also appears to have a unique composition of immunomodulating fructions such as immunoglobulins. Using an advanced low temperature filtrations system our undenatured whey and our whey protein is superior in quality.

Branched Chain Amino Acids

In nature, there are three Branched Chain Amino Acids: L-lsoleucine, L-Leucine and L-Valine. Amino acids are the building blocks of protein. These three are among those considered "essential" because they cannot be manufactured in the body and must be obtained through diet. They have been shown to provide safe nutritional support for individuals seeking optimal lean muscle mass. BCAA's play a principle role in muscle recovery, muscle growth and energy maintenance and must be present in the muscle cells to promote protein synthesis. They help increase the bioavailability of complex carbohydrate intake and are absorbed by the muscle cells for anabolic muscle building activity. There is some encouraging evidence suggesting BCAA supplementation may have beneficial effects on fatigue prevention and enhancing recovery and adaptation. Why we need these special amino acids is simple: scientific evidence shows that branched-chain amino acids may help restore muscle mass following surgery, an injury, or trauma. They also help in people who have liver disease. A general deficiency of protein in the diet can cause a loss of stamina, lowered resistance to infection, slow healing of wounds, weakness, and depression.

Glutamine

Glutamine is the most abundant amino acid in the body. It is crucial for many aspects of healthy body function including maintenance of optimal antioxidant status, building and maintenance of muscle tissue, maintenance of optimal immune function, and repair and maintenance of intestinal tissue. L-Glutamine is highly correlated to muscle protein synthesis. It appears that during stress, whether inflicted on the body through heavy exercise, severe illness or a (viral) infection the body's glutamine requirements increase considerably. With the short-term metabolic stress that is created by acute infections, the body can soon return to normal rates of glutamine use. The muscle glutamine levels are quickly restored and the muscles are not damaged. Unfortunately, with the continuous metabolic stress that results from the chronic infection of HIV disease, the demand for glutamine continues and the concentration of this amino acid in the muscles falls rather rapidly. This results in a decline in the synthesis of muscle tissue and, eventually, a wasting away of the muscles. This, of course, makes glutamine crucial for the prevention of internal decline and wasting. A growing body of evidence suggests that the body's defense system requires increasing amounts of glutamine during stress to respond to health threatening events. In the long term low plasma and muscle glutamine levels may lead to net muscle protein loss and decreased resistance against infections. During an immune response when the immune cells have to increase in number and do their work of destroying pathogens, the rate at which glutamine is used increases dramatically. When the body's supply of glutamine runs short, immune function is compromised. Glutamine also increases the activity of natural killer cells and improves the function of neutrophils. In addition, glutamine is critical for the immune function of the respiratory tract, the genitourinary tract, and the intestinal tract.

Nucleotides

Nucleotides are naturally occurring compounds that are involved in key metabolic processes including energy metabolism and enzymatic reactions. They are the building blocks of deoxyribonucleic acid (DNA) and ribonucleic acid (RNA). Essentially, nucleotides are required by all cells, and are particularly important for cells with rapid turnover including mucosal cells, lymphocytes and macrophages. During stress states, a dietary source is required to promote optimal tissue growth and replication of T-cells. Dietary sources of preformed nucleotides seem to be important for optimal function of the cellular immune response. It has been reported that the absence of dietary nucleotides causes a significant decrease in many specific and non-specific immunologic responses. Nucleotide supplementation has been shown to improve immune function, promote the growth of healthy bacteria in the gut and suppress the growth of gram-negative bacteria in the large intestine. Research in humans and animals has shown that diets lacking dietary nucleotides result in increased susceptibility to infectious agents such as *Candida albicans* and *Staphylococcus aureus*, and may increase risk for gastrointestinal infections. As problems continue to arise with antibiotic-resistant microorganisms, it will become more important for people to strengthen their immune defense system. Nucleotides represent a critical component in the arsenal.

In addition to the key components of the present invention, a conventional blend of vitamins and minerals can be incorporated. Other conventional ingredients to nutrient drinks may be added.

The range of components in the compositions of the present invention are set for in the Table A below:

All values are on a per daily basis. U stands for units of activity.

TABLE A

| COMPONENT RATIOS | | |
|---|---|---|
| | BROAD RANGE | PREFERRED RANGE |
| ANTIOXIDANTS | | |
| SOD lipid or protein carrier | 25 U to 5,000 U SOD | 200 U to 500 U SOD |
| OR | | |
| SOD/Gliadin (preferred) | 25 U to 5,000 U SOD | 200 U to 500 U SOD |
| Beta Glucans | 50 mg to 500 mg | 100 mg to 300 mg |
| Fruit Polyphenols | 25 mg to 500 mg | 25 mg to 100 mg |
| Mitochondrial/ Energy Support | | |
| D-Ribose | 1,000 mg to 5,000 mg | 1,000 mg to 3,000 mg |
| L-Carnitine | 250 mg to 2,000 mg | 300 mg to 1,000 mg |
| Coenzyme Q 10 | 60 mg to 500 mg | 60 mg to 200 mg |
| Agents to Maintain Lean Muscle Mass | | |
| Ornithine Alpha ketoglutarate | 1,000 mg to 8,000 mg | 2,000 mg to 5,000 mg |
| Undenatured whey protein | 5,000 mg to 40,000 mg | 15,000 mg to 25,000 mg |
| Branched Chain Amino Acids | 1,000 mg to 10,000 mg | 3,000 mg to 5,000 mg |
| Nucleotides | 100 mg to 1,000 mg | 100 mg to 500 mg |
| Glutamine | 500 mg 1,000 mg | 1,000 mg to 5,000 mg |

EXAMPLE

The following formulation was blended by conventional blending processes to yield the following composition (on a per day consumption basis). Typically, two one-bottle servings each containing 50% of the defined amounts are taken by the patient.

| Component | Per Day Amount (mg) |
|---|---|
| SOD (as SOD/Gliadin) | *400 → |
| NUCLEOTIDES (as Cytidine, Adenosine, Guanosine and Uridine Monophosphate) | 200 |
| OKG (Ketoglutarate Omithine) | 3,500 ← OKG |
| Glutamine (as L-Glutamine) | 1,000 |
| Beta Glucans (Oat Bran) | 200 |
| Coenzyme Q 10 | 150 |
| Carnitine (L-Camitine Fumarate) | 600 |
| Ribose (D-Ribose) | 1,500 |
| LEUCINE (L-LEUCINE) | 2,000 |
| VALINE (L-VALINE) | 750 |
| ISOLEUCINE (L-ISOLEUCINE) | 750 |

-continued

| Component | Per Day Amount (mg) |
|---|---|
| LYSINE (L-LYSINE) | 500 |
| MCT (Medium Chain Triglycerides) | 500 |
| Fruit Polyphenols (Apple, Cherry, Nectarine, Prune, Pomegranate | 25 |
| LECITHIN (Phosphatidyl Lecithin) | 500 |

*It is 400 units of SOD activity not mg as listed above.

The composition may also contain conventional supplements of Vitamins A, $B_6$, $B_{12}$, C, D, E; Thiamine, Riboflavin, Niacin, Folic Acid, Calcium, Iron, Iodine, Magnesium, Zinc, Selenium, Copper, Chromium, Sodium and Potassium; as well as natural and artificial flavors, vegetable and xanthen gums, undenatured Whey Protein Isotate, etc.

While particular embodiments of the invention have been described, various modifications thereof may be made without departing from the spirit of the present invention and without departing from the invention as claimed.

I claim:

1. A nutritional supplement for treating chronic debilitating diseases to overcome conditions of oxidative stress, lean muscle mass loss and decreased energy comprising in combination:
   1) an orally administrable superoxide dismutase (SOD) in combination with a carrier derived from plants selected from the group consisting of lipids and proteins,
   2) a mitochondrial/energy support component and
   3) Ornithine Alpha Ketoglutarate to decrease lean muscle mass loss.

2. The nutritional supplement of claim 1, wherein SOD is in combination with a protein prolamine carrier derived from cereal.

3. The nutritional supplement of claim 1, wherein SOD is in combination with Gliadin.

4. The nutritional supplement of claim 1, wherein component 2) is selected from the group consisting of D-Ribose, L-Carnitine , and Coenzyme Q10.

5. The nutritional supplement of claim 2, wherein component 2) is selected from the group consisting of D-Ribose, L-Carnitine and Coenzyme Q10.

6. A nutritional supplement for treating chronic deliberating diseases to over come conditions of oxidative stress, lean muscle mass loss and decreased energy comprising, in combination, effective amounts of:
   1) an orally administrable superoxide dismutase (SOD) in a Gliadin carrier,
   2) a mitochondrial/energy support component selected from the group consisting of D-Ribose, L-Carnitine, and Coenzyme Q10, and
   3) Ornithine Alpha Ketoglutarate to decrease lean muscle loss.

7. The nutritional supplement of claim 6 which contains on a daily dosage basis 200 U to 500 U of SOD.

8. The nutritional supplement of claim 6 where component 1) further contains an antioxidant selected from the group consisting of Beta Glucans, Nucleotides and Fruit Polyphenols.

9. The nutritional supplement of claim 6, wherein component 3) further contains a member of the group consisting of Undenatured Whey Protein, Instantized Casein and Branched Chain Amino Acids.

10. The nutritional supplement of claim 6, which further contains a flavoring agent and is readily miscible in water and/or milk.

11. The nutritional supplement of claim 6, which contains on a daily dosage basis:
   200 U to 500 U of component 1),
   300 to 1,000 mg of component 2), and
   2,000 to 5,000 mg of component 3).

* * * * *